(12) United States Patent
Markert et al.

(10) Patent No.: US 6,632,787 B1
(45) Date of Patent: Oct. 14, 2003

(54) CARBONYL COMPOUNDS, METHODS OF MAKING THE SAME, AND THEIR USE AS FRAGRANCES AND FRAGRANCE-ENHANCING ADDITIVES

(75) Inventors: Thomas Markert, Monheim (DE); Ute Lemke, Neuss (DE); Elke Veit, Titz (DE); Theo Ten Pierik, Venlo (NL); Ralph Nemitz, Juechen (DE); Volker Porrmann, Hilden (DE); Marc Speitkamp, Duesseldorf (DE)

(73) Assignee: Cognis Deutschland GmbH & Co. KG, Duesseldorf (DE)

( * ) Notice: Subject to any disclaimer, the term of this patent is extended or adjusted under 35 U.S.C. 154(b) by 0 days.

(21) Appl. No.: 09/831,444

(22) PCT Filed: Oct. 30, 1999

(86) PCT No.: PCT/EP99/08282

§ 371 (c)(1), (2), (4) Date: Aug. 10, 2001

(87) PCT Pub. No.: WO00/27784

PCT Pub. Date: May 18, 2000

(30) Foreign Application Priority Data

Nov. 10, 1998 (DE) ......................................... 198 51 684

(51) Int. Cl.$^7$ ................................................. A61K 7/46
(52) U.S. Cl. ................................. 512/8; 512/25; 512/26; 512/27; 568/303; 568/338; 568/361; 568/365; 568/379
(58) Field of Search ................................. 512/8, 25, 26, 512/27; 568/303, 338, 361, 365, 379

(56) References Cited

U.S. PATENT DOCUMENTS 4,069,258 A    1/1978   Hoffmann et al.

OTHER PUBLICATIONS

Tillet, "Nucleophilic Substitution at Tricoordinate Sulfur", Chemical Reviews, vol. 76, No. 6, (Feb. 1976), pp. 747–772.
Luche, et al., "Reduction of Natural Enones in the Presence of Cerium Trichloride", J.C.S. Chem. Comm., (1978), pp. 601–602.

*Primary Examiner*—Jill Warden
*Assistant Examiner*—Monique T. Cole
(74) *Attorney, Agent, or Firm*—Oblon, Spivak, McClelland, Maier & Neustadt, P.C.

(57) ABSTRACT

Carbonyl compounds derived from the reaction of alkyl cyclopentenols and vinyl ethers are described. The carbonyl compounds described have excellent fragrance properties, and their use as fragrances and/or fragrance-enhancing compounds is also described. Processes for the preparation of the carbonyl compounds are described as well.

15 Claims, No Drawings

CARBONYL COMPOUNDS, METHODS OF MAKING THE SAME, AND THEIR USE AS FRAGRANCES AND FRAGRANCE-ENHANCING ADDITIVES

BACKGROUND OF THE INVENTION

Judging by demand, many natural perfumes are available in totally inadequate quantities. For example, 5,000 kg of rose blossoms are required to produce 1 kg of rose oil. The consequences are a seriously limited annual world production and a high price. Accordingly, it is clear that the perfume industry has a constant need for new perfumes with interesting notes in order to add to the range of naturally available perfumes, to make the necessary adaptations to changing fashion trends and to be able to cover the constantly increasing demand for improvements in the odor of products of everyday use, such as cosmetics and cleaners.

In addition, there is generally a constant demand for synthetic perfumes which can be favorably produced in a consistent quality and which have desirable olfactory properties, i.e. pleasant, close-to-nature and—qualitatively—novel odor profiles of sufficient intensity, and which are capable of favorably influencing the smell of cosmetic products and consumer goods. In other words, there is a constant need for compounds which have characteristic new odor profiles and, at the same time, high staying power, intensity of odor and emanative power.

BRIEF SUMMARY OF THE INVENTION

The present invention relates, in general, to carbonyl compounds with a particular structure, and to a process for their production and their use as perfumes.

It has been found that compounds corresponding to general formula (I) meet the requirements stated above in every respect and may advantageously be used as perfumes with differently nuanced odor notes characterized by high staying power.

In a first embodiment, the present invention relates to carbonyl compounds corresponding to general formula (I):

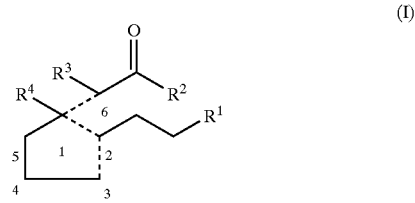

in which $R^1$ is hydrogen or a $C_{1-5}$ alkyl group, $R^2$ and $R^3$ independently of one another represent hydrogen or a $C_{1-3}$ alkyl group, a C=C double bond is present in one of the positions C-1/C-2, C-2/C-3 or C-1/C-6 and $R^4$ is either hydrogen or—if the C=C double bond is in the C-2/C-3 position—is hydrogen or a $C_{1-3}$ alkyl group.

2-(2'-n-hexylcyclopent-2'-en-1'-yl)-acetaldehyde, 2-(2'-n-hexylcyclopent-2'-en-1'-yl)-propionaldehyde and (2-n-hexylcyclopent-2-en-1 -yl)-acetone are most particularly preferred.

The compounds corresponding to formula (I) may be prepared by any of the methods known to the preparative organic chemist. According to the invention, however, they are prepared in particular from special allyl alcohols, the 2-alkylcyclopent-2-en-1-ols, which may optionally contain another alkyl group in the 3-position and which, when reacted with special vinyl ethers, give intermediate products that are accessible to [3,3]-sigmatropic rearrangements. In the case of the rearrangement products, the C=C double bond formed primarily in the five-membered ring may be subsequently shifted towards the carbonyl group.

2-Alkylcyclopent-2-en-1-ones—products generally obtainable commercially under such names as isojasmone, sedamon, cis-jasmone, dijasmone, dihydrojasmone or dihydroisojasmone or by aldol condensation of cyclopentanone with various aldehydes—can be selectively reduced to the corresponding allyl alcohols, the 2-alkylcyclopent-2-en-1-ols, with complex hydrides such as, for example, alkali metal borohydrides or aluminium hydrides, or by Meerwein-Ponndorf reduction with aluminium alcoholates.

The present invention also relates to a process for the production of carbonyl compounds (I) in which alkyl cyclopentenols corresponding to general formula (II):

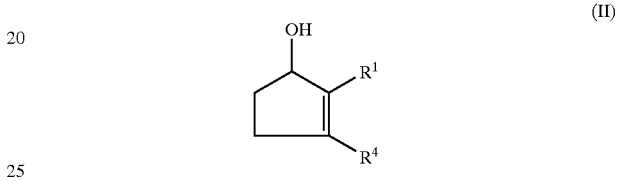

in which $R^1$ and $R^4$ are as defined above, are reacted with vinyl ethers corresponding to general formula (III):

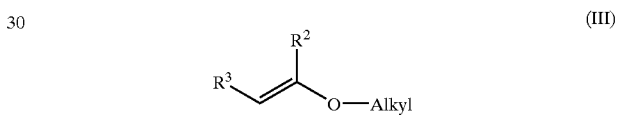

in which $R^2$ and $R^3$ are as defined above. The "Alkyl" moiety in formula (III) is methyl, ethyl, propyl, $C_{4-10}$ alkyl and cycloalkyl.

Examples of suitable vinyl ethers are ethyl vinyl ether, 2-methoxypropene, 1-propenyl ethyl ether, 2-propenyl ethyl ether, cyclohexyl vinyl ether.

DETAILED DESCRIPTION OF THE INVENTION

The compounds (I) are distinguished by a pronounced aldehydic character to their odor with intensive green and fruit notes.

In perfume compositions, the compounds (I) strengthen harmony, emanation and also staying power, the quantities used being adapted to the particular perfume note required taking the other ingredients of the composition into account.

The fact that the carbonyl compounds (I) have aldehydic green-fruity notes was not foreseeable and, hence, is further confirmation of the general experience that the olfactory properties of known perfumes do not allow any definitive conclusions to be drawn as to the properties of structurally related compounds because neither the mechanism of odor perception nor the influence of chemical structure on odor perception has been sufficiently researched, so that it is not normally possible to predict whether modifications to the structure of known perfumes will in fact lead to changes in their olfactory properties or whether these changes will be positive or negative.

Accordingly, the present invention also relates to the use of the compounds (I) as perfumes.

By virtue of their odor profile, the compounds corresponding to formula (I) are also particularly suitable for modifying and enhancing known compositions. Particular emphasis is placed on their extreme intensity of odor which contributes quite generally towards refining the composition.

The compounds corresponding to formula (I) may be combined with many known perfume ingredients, for example other perfumes of natural, synthetic or partly synthetic origin, essential oils and plant extracts. The range of natural fragrances can thus include both high-volatility and also medium-volatility and low-volatility components while the range of synthetic perfumes may include representatives of virtually every class of compounds. Examples are:

(a) natural products, such as tree moss absolue, basil oil, citrus oils, such as bergamot oil, mandarin oil, etc., mastix absolue, myrtle oil, palmarosa oil, patchouli oil, petitgrain oil, wormwood oil, myrrh oil, olibanum oil (b) alcohols, such as farnesol, geraniol, linalool, nerol, phenylethyl alcohol, rhodinol, cinnamic alcohol, sandalore [3-methyl-5-(2,2,3-trimethylcyclopent-3-en-1-yl)-pentan-2-ol], sandela [3-isocamphyl-(5)-cyclohexanol]

(c) aldehydes, such as citral, Helional®, α-hexyl cinnamaldehyde, hydroxycitronellal, Lilial® [p-tert.butyl-α-methyldihydrocinnamalde-hyde], methylnonyl acetaldehyde (d) ketones, such as allylionone, α-ionone, β-ionone, isoraldein, methyl ionone (e) esters, such as allylphenoxyacetate, benzyl salicylate, cinnamyl propionate, citronellyl acetate, citronellyl ethoxylate, decyl acetate, dimethylbenzyl carbinyl acetate, ethyl acetoacetate, hexenyl isobuty-rate, linalyl acetate, methyl dihydrojasmonate, vetiveryl acetate, cyclohexyl salicylate (f) lactones, such as gamma-undecalactone, 1-oxaspiro [4.4]-nonan-2-one and various other components often used in perfumery, such as musk, indole, p-methan-8-thiol-3-one, methyl eugenol, Ambroxan.

It is also remarkable how the compounds corresponding to formula (I) round off and harmonize the odor notes of a broad range of known compositions without unpleasantly dominating them in any way. 2-(2'-n-hexylcyclopent-2'-en-1'-yl)-antaldehyde is particularly emphasized in this regard.

The compounds according to the invention contain chirality centers so that they may exist in various spatial forms. The compounds according to the invention accumulate as mixtures of the corresponding isomers in the course of typical syntheses and are used in this form as perfumes/fragrances.

The compounds according to the invention or mixtures thereof may be used in perfume compositions in quantities of 1 to 70% by weight, based on the mixture as a whole. Mixtures of compounds (I) according to the invention and compositions of this type may be used both for perfuming cosmetic preparations, such as lotions, creams, shampoos, soaps, emollients, powders, aerosols, toothpastes, mouthwashes, deodorants, and also in alcohol-based perfumery (for example colognes, toilet waters, extracts). The compounds according to the invention or mixtures thereof may also be used for perfuming commercial products, such as detergents, fabric softeners and textile treatment preparations. For perfuming these various products, the compositions are added in an olfactorily effective quantity, more particularly in a concentration of 0.05 to 2% by weight, based on the product as a whole. However, these values are not intended to represent limits because the experienced perfumer can also obtain effects with even lower concentrations or can build up new complexes with even higher doses.

EXAMPLE

A) Precursors

Example 1

Preparation of "Isojasmone"

(2-n-hexyl-2-cyclopenten-1-one and 2-n-hexylidenecyclopentan-1-one)

Materials 210 g (2.5 moles) cyclopentanone
280 g (2.8 moles) n-hexanal
280 ml (0.25 mole) KOH solution, 5%
280 ml cyclohexane
300 g (0.3 mole) sulfuric acid, 5%
0.17 g p-toluenesulfonic acid Method The reaction was carried out in a 2-liter face-ground flask with built-in internals and a turbine impeller (1000 r.p.m.). The 5% KOH and the cyclohexane were introduced into the reactor first—under nitrogen at 15° C. A solution of cyclopentanone and hexanal was added dropwise with stirring over a period of 2 hours at 15 to 20° C. After stirring for 2 hours, the reaction mixture was neutralized with the sulfuric acid. The reaction mixture was then transferred to a separation funnel and the phases were separated. The aqueous phase was discarded and the cyclohexane phase was washed with dist. water until neutral. Without drying, the p-toluenesulfonic acid was added to the organic phase which was then heated under reflux on a water separator for the azeotropic distillation of ca. 50 ml water. Another 0.8 g of p-toluenesulfonic acid was added and another 7 ml water were removed from the circuit. Working up:

The cyclohexane was distilled off and the 400 g of black residue were distilled through an oil-heated thin-layer evaporator (jacket temperature 115–120° C./0.1 mbar).

In the subsequent fractional distillation in a spinning-band column, the product was isolated as an isomer mixture (compounds with an exo- and endocyclic double bond) in a yield of 45% of the theoretical.

Example 2

Isomerization of the 2-n-hexylidene Cyclopentanone to 2-n-hexylcyclopent-2-en-1-one (According to J. G. Tillet, Chem. Rev. 76, 747 (1976)]

Materials 332 g (2 moles) isojasmone (isomer mixture of Example 1)
2 l 1-butanol
0.2 l conc. hydrochloric acid Method The isojasmone and n-butanol were introduced into a 4-liter three-necked flask equipped with a KPG stirrer, a dropping funnel, a jacketed coil condenser and a temperature probe and the hydrochloric acid was added dropwise at room temperature. A slight increase in temperature was observed. The reaction mixture was stirred for 3 hours at ca. 100° C. and then diluted with diethyl ether.

Working Up

The organic phase was separated off and washed with water, bicarbonate solution and water and then dried over magnesium sulfate, filtered and concentrated. 329.5 g of residue were weighed out. The material was distilled in a high vacuum in a 10 cm Vigreux column, giving 171.9 g of 2-n-hexylcyclopent-2-en-1-one with a purity of more than 99%. The yield amounted to 51.8% of the theoretical.

Example 3

Reduction of Isojasmone to Isojasmol (According to J. L. Luche, L. Rodriguez-Hahn, P. Grabbe, J.S.C. Chem. Comm., 1978, pp. 601–2)

Materials

I) 167.8 g (1 mole) isojasmone (prepared in accordance with Example 2 or commercial product, from example from Quest)

II) 373 g (1 mole) cerium(III) chloride heptahydrate

III) 38 g sodium borohydride

IV) 1.5 l methanol

Components I, II and IV were mixed at room temperature in a 4-liter four-necked flask. Component III was added in portions with vigorous stirring over a period of 3 hours, followed by stirring for 2 hours at room temperature.

Working Up

Ca. 1 liter water was added to the mixture which was then extracted 4 times with cyclohexane. The organic phase was dried over sodium sulfate and concentrated in a rotary evaporator.

The residue of 161.3 g of reaction mixture was distilled in a 15 cm Vigreux column. 136.1 g of product with a gas chromatographically determined purity of ca. 90% (73% of the theoretical) were obtained and were used without further purification for subsequent syntheses.

Example 4

Preparation of 3-methyl-2-n-heptylcyclopent-2-en-1-one from the Henkel Perfume "Aldehyd 11/11"

Materials 170 g (1 mole) Aldehyd 11/11 (mixture of methyloctyl acetaldehyde and undecanal)

125 g (1.2 mole) malonic acid 4 g ammonium acetate 400 ml toluene

Method

All the components were rapidly combined in a 1-liter three-necked flask equipped with a stirrer, internal thermometer and Dean-Starck water separator and heated with vigorous stirring to reflux temperature. After 3 hours, 18 ml water had been azeotropically distilled off and separated off. Ca. 280 g toluene were then distilled off at an oil bath temperature of 50° C. and the residue was distilled in a short-path still (jacket temperature 205° C., 0.03 mbar). 115 g (54.3% of the theoretical) of 4-methyldodec-3-enoic acid were obtained.

115 g of 85% sulfuric acid were added with stirring to the 115 g of 4-methyldodec-3-enoic acid in a 500 ml three-necked flask and the mixture was heated for 4 hours to 90° C. For working up, the reaction mixture was carefully stirred into 500 ml water, extracted three times with 250 ml ether and the combined ether phases were washed with bicarbonate solution until neutral, dried over sodium sulfate and concentrated in a rotary evaporator. The residue of 92 g was distilled in a bulb-tube still at 180° C./0.03 mbar pressure, 66 g (57.4% of the theoretical) of 5-methyl-5-n-octylbutyrolactone and 5 g residue being obtained.

In a 1-liter three-necked flask, 200 g of polyphosphoric acid (Fluka) were heated with stirring under nitrogen to 100° C. and 63.6 g (0.3 mole) of 5-methyl-5-n-octyl butyrolactone were added dropwise over a period of 45 minutes. The mixture was stirred for 1.5 hours at 100° C. and then cooled. The product was extracted with 3×150 ml diethyl ether, washed with bicarbonate solution until neutral, dried over sodium sulfate and concentrated in a rotary evaporator. 60 g residue (GC purity 78%) were predistilled in a bulb-tube still (furnace temperature 150° C., 0.03 mbar). The 58 g obtained were distilled in a 15 cm long Vigreux column and the main runnings of 32.5 g (purity 95%) were fractionated in a spinning-band column. 20.8 g of 100% pure 3-methyl-2-n-heptyl-2-cyclopenten-1-one (Bp. 74–76° C./0.08 mbar) were obtained. Odor description: jasmone, diffusive, flowery, celery note.

B) Compounds According to the Invention

Example 5

Reaction of Isojasmol to 2-(2'-n-hexylcyclopent-2'-en-1'-yl)-acetaldehyde

Materials 433.1 g (2 moles) isojasmol (prepared in accordance with Example 3)

173.1 g (2.4 moles) ethyl vinyl ether (99%, Fluka)

18 g (0.24 mole) propionic acid

Method

The components were introduced under nitrogen into a 2-liter V2A steel autoclave insert and stirred in an autoclave for 4 hours at 180° C./50 bar nitrogen. Another 18 g of propionic acid were then added to the reaction mixture, followed by stirring for another 4 hours at 200° C./60 bar nitrogen. As was readily established by GC, a number of intermediate products were formed at 180° C. and were converted at 200° C. partly into the educt isojasmol and partly into the required product (2 main components).

Working up

After low-boiling components had been distilled off, 459.2 g of crude product were used for distillation in a high vacuum in a spinning-band column. 79 g of main runnings distilled over at head temperatures of 64–73° C./.04 mbar (2 isomers, GC purity 60%). This low purity was olfactorily acceptable. Odor description: aldehydic, green, ozone, flowery, fruity, water melon, fatty.

Example 6

Reaction of Isojasmol to 2-(2'-n-hexylcyclopent-2'-en-1'-yl)-propionaldehyde

Materials 84.0 g (0.5 mole) isojasmol (prepared in accordance with Example 3)

56.0 g (0.65 mole) ethyl-1-propenyl ether (Fluka)

1.5 g propionic acid (Merck)

Method

As in Example 5, the components were first introduced into a V2aA steel autoclave insert, heated to 210° C. under an initial nitrogen pressure of 10 bar and stirred for 8 hours. The pressure rose to 30 bar.

Working Up

The crude product was freed from excess ether in a rotary evaporator and 95.4 g of a dark brown liquid were distilled in a high vacuum through a 30 cm packed column (Brunswick coils). The main runnings of 24.5 g of a light yellow liquid (Bp. 62–93° C./0.08 mbar) were fractionated in a spinning-band column. 15.4 g of 2-(2-n-hexylcyclopent-2-en-1-yl)-propionaldehyde (Bp. 60–64° C./0.04 mbar) were obtained. The gas chromatographic purity was 93%.

Odor description: green, aldehydic, flowery, emanative (diffusive), fruity, melon, ozone.

Example 7

Reaction of isojasmol to (2-n-hexylcyclopent-2-en-1-yl)-acetone

Materials
- 84.0 g (0.5 mole) isojasmol (prepared in accordance with Example 3)
- 56.0 g (0.78 mole) 2-methoxypropene (Janssen)
- 1,5-propionic acid (Merck)

Method

The components were introduced into a V2A steel autoclave insert under 10 bar nitrogen and heated with stirring for 8 hours to 210° C. (30 bar working pressure).

Working Up

The crude product was freed from excess ether and the residue, 85.8 g of a dark brown liquid, was used for distillation in a high vacuum in a 30 cm long column packed with Brunswick coils. 37.3 g of a light yellow liquid (Bp. 80–94° C./0.08 mbar) were obtained as main runnings and were fractionated in a spinning-band column. 33.4 g of a light green liquid, Bp. 85–87° C./0.06 mbar, were obtained. Odor description: flowery, diffusive, spicy, celery note, mushroomy.

Example 8

Preparation of (2'-n-hexylcyclopentylidene)-acetaldehyde from 2-n-heylcyclopentan-1-one Step 1
Materials
- 83.9 g (0.5 mole) jasmatone (2-n-hexylcyclopentan-1-one; Quest)
- 111.0 g (0.75 mole) triethyl orthoformate
- 101.8 mg potassium hydrogen sulfate
- 500 ml ethanol, water-free Apparatus
- 1-liter stirred reactor, KPG stirrer, thermometer, reflux condenser Method The apparatus was dried and heated with a hot air blower while a constant stream of nitrogen was passed through (25 ml/min.). The jasmatone was introduced first in 200 ml. abs. ethanol, after which the triethyl orthoformate, the potassium hydrogen sulfate and the remaining 300 ml of ethanol were added. The withdrawal of educt and the formation of several products was monitored by GC. After 5 hours, the reaction was terminated and the reaction mixture was neutralized by addition of a small quantity of sodium methanolate solution. The mixture was combined with another two reaction mixtures prepared under the same conditions and the total of 411.5 g of crude product was distilled in a 20 cm long Vigreux column. 252.3 g of jasmatone diethyl ketal (1,1-diethoxy-2-n-hexyl cyclopentane) (GC purity 97% (2 peaks), Bp. 95–98° C./0.08 mbar) were obtained as main runnings.

Step 2
Materials
- 31.22 g (1.34 mole) 1,1-diethoxy-2-n-hexyl cyclopentane (prepared in accordance with step 1)
- 144.9 g (2 moles) ethyl vinyl ether
- 115 ml zinc (II) chloride solution, 10% in ethyl acetate Apparatus
- 1-liter stirred reactor, reflux condenser, dropping funnel, thermometer Method The 1,1-diethoxy-2-n-hexyl cyclopentanone and the zinc chloride solution were introduced first with stirring and heated to 40–45° C. The ethyl vinyl ether was continuously added to this mixture over a period of 2 hours. After the addition, the mixture was stirred for 3 hours at 40–50° C.

Working Up

The reaction mixture was washed twice with 0.1 molar sodium hydroxide solution and twice with water, dried over sodium sulfate and concentrated in a rotary evaporator. Distillation in a 20 cm long Vigreux column produced 61.5 g of ca. 62% 1-(2,2-diethoxyethyl)-1-ethoxy-2-hexyl cyclopentane (2 diastereomers, Bp. 130–140° C./0.04 mbar).

Step 3
Materials
- 61.5 g (0.121 mole) 1-(2,2-diethoxyethyl)-1-ethoxy-2-hexyl cyclopentane (prepared in accordance with step 2)
- 18.7 g (0.41 mole) formic acid
- 5.0 g (0.074 mole) sodium formate
- 8.0 g (0.443 mole) water, demineralized Apparatus
- 250 ml stirred reactor, PT 100 (stainless steel temperature sensor), reflux condenser, dropping funnel Method The formic acid/sodium formate buffer was introduced first and heated to reflux temperature (113° C.). The 61.5 g of 1-(2,2-diethoxyethyl)-1-ethoxy-2-hexylcyclopentane were continuously added with stirring over a period of 1.15 hours at reflux temperature. The mixture was kept at reflux temperature (now 78° C.) for another 2 hours. Working up:

The mixture was stirred into 200 ml of ice water and the organic phase was separated off. The aqueous phase was then extracted with 3×100 ml diethylether and the combined organic phases were washed until neutral, dried over magnesium sulfate and concentrated in a rotary evaporator. The fractionation of 55 g of crude product in a spinning-band column produced product fractions with different GC purities (total quantity of the fractions: 38.5 g).

Fraction 3 with a composition of 49/15/19 GC% (Bp. 63–82° C./0.08 mbar; 2-n-hexylcyclopentylidene acetaldehyde and isomers with a double bond in the 1- or 2-position) were olfactorily evaluated as comparable with the odor of the compound of Example 6: green, aldehydic, fresh, less melon and ozone than in Example 6. A fatty note was additionally detected in the other fractions.

What is claimed is:

1. A compound corresponding to general formula (I):

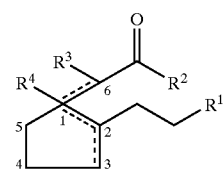

wherein $R^1$ represents a hydrogen atom or a $C_{1-5}$ alkyl group, wherein each of $R^2$ and $R^3$ independently represents a hydrogen atom or a $C_{1-3}$ alkyl group, wherein a carbon-carbon double bond is present in a position selected from the group consisting of $C^1/C^2$, $C^2/C^3$ and $C^1/C^6$; and wherein $R^4$ represents a hydrogen atom or a $C_{1-3}$ alkyl group when the carbon-carbon double bond is present in the $C^2/C^3$ position.

2. The compound according to claim 1, wherein $R^1$ represents a $C_4$ alkyl group, the carbon-carbon double bond is present in the $C^2/C^3$ position, and each of $R^2$, $R^3$ and $R^4$ represents a hydrogen atom.

3. The compound according to claim 1, wherein $R^1$ represents a $C_4$ alkyl group, the carbon-carbon double bond is present in the $C^2/C^3$ position, $R^3$ represents a methyl group, and each of $R^2$ and $R^4$ represents a hydrogen atom.

4. The compound according to claim 1, wherein $R^1$ represents a $C_4$ alkyl group, the carbon-carbon double bond is present in the $C^2/C^3$ position, $R^2$ represents a methyl group, and each of $R^3$ and $R^4$ represents a hydrogen atom.

5. A process for preparing compounds corresponding to general formula (I):

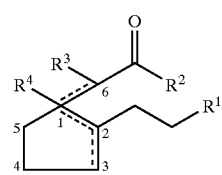
(I)

wherein $R^1$ represents a hydrogen atom or a $C_{1-5}$ alkyl group, wherein each of $R^2$ and $R^3$ independently represents a hydrogen atom or a $C_{1-3}$ alkyl group, wherein a carbon-carbon double bond is present in a position selected from the group consisting of $C^1/C^2$, $C^2/C^3$ and $C^1/C^6$; and wherein $R^4$ represents a hydrogen atom or a $C_{1-3}$ alkyl group when the carbon-carbon double bond is present in the $C^2/C^3$ position;

said process comprising:

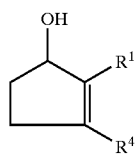
(II)

(a) providing an alkyl cyclopentenol according to general formula (II):
wherein $R^1$ and $R^4$ are as defined above;
(b) providing a vinyl ether according to general formula (III):

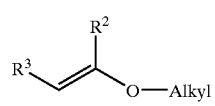
(III)

wherein $R^2$ and $R^3$ are as defined above, and wherein the Alkyl group represents a linear or branched $C_{1-10}$ alkyl or cycloalkyl group; and
(c) reacting the alkyl cyclopentenol and the vinyl ether.

6. The process according to claim 5, wherein $R^1$ represents a $C_{1-5}$ alkyl group.

7. The process according to claim 5, wherein $R^1$ represents a $C_4$ alkyl group, and each of $R^2$, $R^3$ and $R^4$ represents a hydrogen atom.

8. The process according to claim 5, wherein $R^1$ represents a $C_4$ alkyl group, $R^3$ represents a methyl group, and each of $R^2$ and $R^4$ represents a hydrogen atom.

9. The process according to claim 5, wherein $R^1$ represents a $C_4$ alkyl group, $R^2$ represents a methyl group, and each of $R^3$ and $R^4$ represents a hydrogen atom.

10. A method of enhancing the fragrance properties of a composition, said method comprising:
(a) providing a composition with fragrance properties to be enhanced;
(b) providing the compound according to claim 1; and
(c) combining a fragrance-enhancing effective amount of the compound and the composition.

11. A method of providing a fragrance to a composition, said method comprising:
(a) providing a composition to be enhanced with a fragrance;
(b) providing the compound according to claim 1, and
(c) combining a fragrance-providing effective amount of the compound and the composition.

12. A perfume composition comprising a compound according to general formula (I):

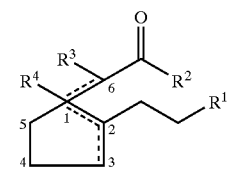
(I)

wherein $R^1$ represents a hydrogen atom or a $C_{1-5}$ alkyl group, wherein each of $R^2$ and $R^3$ independently represents a hydrogen atom or a $C_{1-3}$ alkyl group, wherein a carbon-carbon double bond is present in a position selected from the group consisting of $C^1/C^2$, $C^2/C^3$ and $C^1/C^6$; wherein $R^4$ represents a hydrogen atom or a $C_{1-3}$ alkyl group when the carbon-carbon double bond is present in the $C^2/C^3$ position, and wherein the compound is present in an amount of from 1 to 70% by weight, based on the weight of the perfume composition.

13. The perfume composition according to claim 12, wherein $R^1$ represents a $C_4$ alkyl group, the carbon-carbon double bond is present in the $C^2/C^3$ position, and each of $R^2$, $R^3$ and $R^4$ represents a hydrogen atom.

14. The perfume composition according to claim 12, wherein $R^1$ represents a $C_4$ alkyl group, the carbon-carbon double bond is present in the $C^2/C^3$ position, $R^3$ represents a methyl group, and each of $R^2$ and $R^4$ represents a hydrogen atom.

15. The perfume composition according to claim 12, wherein $R^1$ represents a $C_4$ alkyl group, the carbon-carbon double bond is present in the $C^2/C^3$ position, $R^2$ represents a methyl group, and each of $R^3$ and $R^4$ represents a hydrogen atom.

* * * * *